US011013677B2

United States Patent
Dogo-Isonagie et al.

(10) Patent No.: US 11,013,677 B2
(45) Date of Patent: May 25, 2021

(54) METHODS AND COMPOSITIONS TO REDUCE STAINING FOR ANTIBACTERIAL ORAL CARE COMPOSITIONS

(71) Applicant: Colgate-Palmolive Company, New York, NY (US)

(72) Inventors: Cajetan Dogo-Isonagie, Highland Park, NJ (US); Paloma Pimenta, Staten Island, NY (US); Shira Pilch, Highland Park, NJ (US); Om Patel, Edison, NJ (US); Elizabeth Vasquez, South Bound Brook, NJ (US); Michael North, Middlesex, NJ (US)

(73) Assignee: Colgate-Palmolive Company, New York, NY (US)

( * ) Notice: Subject to any disclaimer, the term of this patent is extended or adjusted under 35 U.S.C. 154(b) by 39 days.

(21) Appl. No.: 16/395,296

(22) Filed: Apr. 26, 2019

(65) Prior Publication Data

US 2020/0337970 A1 Oct. 29, 2020

(51) Int. Cl.
| | | |
|---|---|---|
| *A61K 45/06* | (2006.01) | |
| *A61K 6/00* | (2020.01) | |
| *A61Q 11/00* | (2006.01) | |
| *A61K 8/44* | (2006.01) | |
| *A61K 8/55* | (2006.01) | |
| *A61K 8/43* | (2006.01) | |

(52) U.S. Cl.
CPC .................. *A61K 8/44* (2013.01); *A61K 8/43* (2013.01); *A61K 8/55* (2013.01); *A61Q 11/00* (2013.01)

(58) Field of Classification Search
CPC .. A61Q 11/00; A61Q 17/005; A61K 2300/00; A61K 8/44; A61K 2800/58; A61K 2800/92; A61K 9/08; A61K 45/06
See application file for complete search history.

(56) References Cited

U.S. PATENT DOCUMENTS

| | | | |
|---|---|---|---|
| 4,118,473 A | 10/1978 | Gaffar et al. | |
| 5,158,763 A | 10/1992 | Gaffar et al. | |
| 5,695,745 A | 12/1997 | Barton et al. | |
| 9,408,794 B2 | 8/2016 | Lewus et al. | |
| 9,532,932 B2 | 1/2017 | Prencipe et al. | |
| 9,565,857 B2 | 2/2017 | Raad et al. | |
| 9,980,890 B2 | 5/2018 | Pan et al. | |
| 10,238,896 B2 | 3/2019 | Myers et al. | |
| 2010/0136069 A1* | 6/2010 | Deckner ................ A61Q 11/00 424/401 |
| 2011/0104179 A1 | 5/2011 | Reynolds et al. | |
| 2017/0151158 A1 | 6/2017 | Myers et al. | |
| 2018/0100083 A1* | 4/2018 | Gizaw .................. C11D 17/049 |

FOREIGN PATENT DOCUMENTS

| | | |
|---|---|---|
| EP | 0026252 | 4/1981 |
| FR | 2281107 | 3/1976 |
| IT | MI20100149 | 11/2011 |
| JP | 2003-146908 | 5/2003 |
| WO | 1993/016681 | 9/1993 |
| WO | 2005/094765 | 10/2005 |

OTHER PUBLICATIONS

ITMI20100149A1, Lastri Ilaria, "Composition for Oral Hygiene Containing Chore-Xidine and a System to Prevent the Formation of Dark Pigments on the Surface of Oral Teeth and Mu-Things," English language machine translation, Espacenet, date obtained: Jan. 21, 2020, 9 pages <https://worldwide.espacenet.com/patent/search/fam ily/042634928/publication/ITMI20100149A1?q= ITMI20100149A1>.
JP2003146908, Rohto Pharma, "Aqueous Composition," May 21, 2003, English language machine translation, Espacenet, date obtained: Apr. 24, 2020, 47 pages <https://worldwide.espacenet.com/patent/search/family/019159314/publication/JP2003146908A?q= JP2003146908>.

* cited by examiner

*Primary Examiner* — Tracy Liu

(57) ABSTRACT

A method of reducing staining by an oral care composition, including providing an effective amount of a metal chelator, wherein the oral care composition includes chlorhexidine.

4 Claims, No Drawings

METHODS AND COMPOSITIONS TO REDUCE STAINING FOR ANTIBACTERIAL ORAL CARE COMPOSITIONS

BACKGROUND

Oral care composition commonly include a variety of antibacterial and/or antimicrobial agents to promote oral hygiene and health. Chlorhexidine (CHX) is often the antimicrobial agent of choice as it combines superior anti-plaque and anti-gingivitis properties with an excellent safety profile. However, CHX is also known to lead to the staining or discoloration of dental surfaces.

Accordingly, there is a desire for oral care compositions and methods to reduce staining for oral care compositions that use CHX.

BRIEF SUMMARY

This summary is intended merely to introduce a simplified summary of some aspects of one or more implementations of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a method of reducing staining by an oral care composition, including providing an effective amount of a metal chelator, wherein the oral care composition comprises chlorhexidine.

The oral care composition may include about 5 weight % or less metal chelator, based on a total weight of the oral care composition.

The oral care composition may include about 1 weight % or less metal chelator, based on a total weight of the oral care composition.

The oral care composition may include about 0.5 weight % or less metal chelator, based on a total weight of the oral care composition.

The oral care composition may include about 0.01 weight % to about 0.5 weight % chlorhexidine, based on a total weight of the oral care composition.

The metal chelator may include glutamic acid.

The metal chelator may include aspartic acid.

The metal chelator may include at least one of glutamic acid, aspartic acid, aminotris(methylenephosphonic acid) (ATMP), polyaspartic acid, and imminodisuccinic acid.

The metal chelator may be an iron chelator and may have a higher iron affinity than chlorhexidine.

The metal chelator may have a $Fe^{3+}$ binding constant of 10 or more.

The oral care composition may be applied to a tooth surface, and an amount of staining of the tooth surface by the oral care composition may be less than an amount of staining by a similar oral care composition without the effective amount of a metal chelator.

The oral care composition may be applied at least daily, and the amount of staining may be less after at least one of 1 day, 2 days, 1 week, 2 weeks, 3 weeks, 4 weeks, 1 month, and 2 months of application, when compared to a similar oral care composition without the effective amount of the metal chelator.

The foregoing and/or other aspects and utilities embodied in the present disclosure may also be achieved by providing a method of reducing staining by an oral care composition including chlorhexidine, including providing an effective amount of one or more iron chelators in the oral care composition, wherein at least one of the one or more metal chelators has a higher affinity for iron than chlorhexidine.

The one or more metal chelators may include at least one of glutamic acid, aspartic acid, aminotris(methylenephosphonic acid) (ATMP), polyaspartic acid, and imminodisuccinic acid.

At least one of the one or more metal chelators may have a $Fe^{3+}$ binding constant of 10 or more, 11, or more, or 12 or more.

The oral care composition may include about 5 weight % or less of the one or more metal chelators, based on a total weight of the oral care composition.

The foregoing and/or other aspects and utilities embodied in the present disclosure may also be achieved by providing an oral care composition, including from about 0.01 weight % to about 0.20 weight % chlorhexidine, based on a total weight of the oral care composition; and an effective amount of metal chelator.

The metal chelator may be an iron chelator with a higher iron affinity than chlorhexidine and the metal chelator may have a $Fe^{3+}$ binding constant of about 10 or more, 11 or more, or 12 or more.

The metal chelator may include at least one of glutamic acid, aspartic acid, aminotris(methylenephosphonic acid) (ATMP), polyaspartic acid, and imminodisuccinic acid.

The oral care composition may further include one or more additional oral care ingredients selected from: a carrier, a humectant, surfactants, polymers, thickeners, antioxidants, preservatives, flavoring agents, sweeteners, colorants, pH modifiers, anti-calculus agents, fluoride sources, and wherein all the ingredients of the oral care composition may be orally acceptable.

The foregoing and/or other aspects and utilities embodied in the present disclosure may be achieved by providing an oral care composition substantially as hereinbefore described, with reference to the examples and excluding, if any, comparative examples.

DETAILED DESCRIPTION

Reference will now be made in detail to the various implementations in the present disclosure, examples of which may be illustrated in any accompanying drawings and figures. The various implementations are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the various implementations.

Throughout the specification and claims, the following terms take the meanings explicitly associated herein, unless the context clearly dictates otherwise. Phrases, such as, "in an implementation," "in certain implementations," and "in some implementations" as used herein do not necessarily refer to the same implementation(s), though they may. Furthermore, the phrases "in another implementation" and "in some other implementations" as used herein do not necessarily refer to a different implementation, although they may. As described below, various implementations may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes implementations containing A, B, or C, multiple examples of A, B, or C, or combinations of A/B, A/C, B/C, A/B/B/B/B/C, A/B/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, component, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5% to 6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Unless otherwise specified, all percentages and amounts expressed herein and elsewhere in the specification should be understood to refer to percentages by weight. The amounts given are based on the active weight of the material.

With regard to procedures, methods, techniques, and workflows that are in accordance with some implementations, some operations in the procedures, methods, techniques, and workflows disclosed herein may be combined and/or the order of some operations may be changed.

While is it well known that oral care compositions including chlorhexidine (CHX) may lead to staining or discoloration of teeth after extended use, the mechanism for this effect is not well understood. However, the present inventors have surprisingly discovered compositions and methods to reduce staining for oral care compositions including chlorhexidine (CHX).

While not intending to be bound by any particular theory, the inventors believe that at least a portion of the staining caused by CHX is due to its interaction with metals to form colored complexes. CHX has a strong ability to bind to teeth and gum surfaces, which enhances its effectiveness as an antimicrobial. However, CHX also has an affinity to complex with metals, such as iron. Accordingly, staining may be, at least partially, caused by the complexing of CHX with metals as it binds to teeth surfaces. The source of metal can be from diet or from blood, especially for sufferers of gingivitis who are prone to bleeding from the gums.

The inventors have surprisingly discovered a method of reducing the staining associated with oral care compositions including chlorhexidine, including providing an effective amount of a metal chelator with the oral care composition. In one implementation, the oral care composition includes an effective amount of a metal chelator.

As used herein, the term "effective amount" refers to an amount of a compound or composition sufficient to significantly induce a positive benefit, preferably an oral health benefit, but low enough to avoid serious side effects, i.e., to provide a reasonable benefit to risk ratio, within the sound judgment of a person having ordinary skill in the art. For example, the oral care composition may include an amount of metal chelator effective to reduce an amount of staining caused by the use of CHX. In another implementation, the oral care composition may include an amount of metal chelator effective to reduce an amount of staining caused by the use of CHX as compared to an oral care composition not including the effective amount of metal chelator. For example, when applied to a tooth surface, an amount of staining of the tooth surface by the oral care composition including the effective amount of metal chelator is less than an amount of staining by a similar oral care composition without the effective amount of a metal chelator. For comparison purposes, the oral care composition may be applied at least daily for 2 weeks. In other implementations, the oral care composition is applied at least daily for 2 days, 3 days, 4, days, 1 week, 2 weeks, 3 weeks, 4 weeks, 1 month, or 2 months.

While not bound by theory, the inventors believe that, by providing a metal chelator, an amount of metal ions available to complex with CHX is reduced, thus reducing CHX-based staining. For example, CHX-iron complexes are believed to cause much of the CHX-based staining in teeth. Accordingly, in one implementation, the metal chelator is an iron chelator. In another implementation, the metal chelator has a higher metal affinity than CHX. For example, the iron chelator may have a higher iron binding constant than CHX in order to prevent metal ions from binding with the CHX. $Fe^{3+}$ may be the main form of free iron (Fe) present in the mouth. Accordingly, in some implementations, the metal chelator has a higher $Fe^{3+}$ binding constant than CHX. In other implementations, the metal chelator has a higher affinity for $Fe^{3+}$ than CHX.

EXAMPLES

Aspects of the present disclosure may be further understood by referring to the following examples. The examples are illustrative, and are not intended to be limiting.

Table 1 is an exemplary listing of metal chelators according to implementations of the present disclosure. In particular, the iron chelators illustrated in Table 1 have a higher affinity for iron than CHX, as evidenced by their high $Fe^{3+}$ bonding constants (log K). ATMP is aminotris(methylenephosphonic acid).

TABLE 1

| Metal Chelator | $Fe^{3+}$ binding constant (logK) |
|---|---|
| Glutamic acid | 12.1 |
| Aspartic acid | 11.4 |
| ATMP | 15.87 |
| Polyaspartic acid | 18.5 |
| Imminodisuccinic acid | 15.2 |

Example 1 below illustrates the ability of exemplary metal chelators to reduce CHX-based staining. In particular, the metal chelators of Table 1 were tested in a bovine enamel model to evaluate their ability to reduce CHX-based staining.

Example 1

A bovine enamel model was used to mimic CHX staining. The bovine teeth samples were kept hydrated until use. Baseline (L*, a*, and b*) measurements were taken of the samples before treatment using a spectroshade. The samples were then placed in a solution representing each of the treatments of Table 2 and then in artificial saliva. This cycle of soaking in the treatment and in artificial saliva was then repeated 14 times for each sample, with spectroshade measurements taken every two cycles immediately after soaking in the artificial saliva step (the samples were dabbed dry before measurements). Control samples soaked in FeCl3 alone and FeCl3+CHX solutions were also done.

The L*, a*, and b* values were used to calculate the change in whiteness (ΔW*) for each tooth after treatment as compared to the baseline values using Formulas (1) and (2) below.

$$W^* = ((a^*-0)^2 + (b^*-0)^2 + (L^*-100)^2)^{1/2} \quad \text{Formula (1)}$$

$$\Delta W^* = W^*\text{treated} - W^*\text{baseline} \quad \text{Formula (2)}$$

Table 2 illustrates the ΔW* for two representative metal chelators of Table 1. The more positive the value of ΔW*, the darker the tooth color is.

TABLE 2

| Treatment | Cycle 0 | Cycle 4 | Cycle 6 | Cycle 8 | Cycle 10 | Cycle 14 |
|---|---|---|---|---|---|---|
| FeCl₃ + CHX | 0 | 3.65 | 5.46 | 6.45 | 6.92 | 8.24 |
| FeCl₃ alone | 0 | 1.31 | 0.83 | 0.90 | 0.64 | 0.78 |
| FeCl₃ + CHX + ATMP | 0 | 0.97 | 1.50 | 1.37 | 2.42 | 2.33 |
| FeCl₃ + CHX + IDA | 0 | 1.46 | 1.67 | 2.89 | 2.78 | 4.06 |

As illustrated in Table 2, the interaction of iron and CHX created stained teeth. However, the incorporation of metal chelators to the system reduced the amount of CHX-based staining.

In particular, as illustrated in Table 2, Aminotris(methylenephosphonic acid) (ATMP) and Imminodisuccinic acid (IDA) decreased the amount of teeth staining caused by CHX when exposed to an iron solution. ATMP performed better at every cycle compared to IDA. While not bound in theory, the inventors believe this may be due to the chemical structure of ATMP having phosphonate compared to the carboxylic acids present in the other metal chelators.

The method of the present disclosure may also be embodied as an oral care composition. In one implementation, an oral care composition, may include chlorhexidine and an effective amount of a metal chelator.

The oral care composition may include from about 0.01 weight % to about 0.50 weight % chlorhexidine, based on the total weight of the oral care composition. For example, the oral care composition may include from about 0.01 weight % to about 0.2 weight % chlorhexidine. In other implementations, the oral care composition may include 0.5 weight % or less, 0.4 weight % or less, 0.3 weight % or less, 0.2 weight % or less, or 0.1 weight % or less, chlorhexidine.

The metal chelator may include one or more metal chelators. The metal chelator may include at least one of glutamic acid, aspartic acid, aminotris(methylenephosphonic acid) (ATMP), polyaspartic acid, and imminodisuccinic acid.

In one implementation, the metal chelator includes glutamic acid. In another implementation, the metal chelator includes aspartic acid.

In other implementations, the metal chelator may include polyphosphates, such as sodium tripolyphosphate (STPP) and tetrasodium pyrophosphate.

The oral care composition may include 5.0 weight % or less metal chelator, based on the total weight of the oral care composition. For example, the oral care composition may include from about 0.10 weight % to about 5.0 weight % metal chelator, from about 0.50 weight % to about 5.0 weight % metal chelator, from about 1.0 weight % to about 5.0 weight % metal chelator, from about 1.50 weight % to about 5.0 weight % metal chelator, from about 2.0 weight % to about 5.0 weight % metal chelator, from about 2.50 weight % to about 5.0 weight % metal chelator, and/or from about 3.0 weight % to about 5.0 weight % metal chelator.

In other implementations, the oral care composition may include 4.50 weight % or less, 4.0 weight % or less, 3.50 weight % or less, or 3.0 weight % or less, metal chelator.

The metal chelator may have a higher metal affinity than CHX. For example, the metal chelator may have a higher iron affinity than CHX. The metal chelator may be an iron chelator and may have a $Fe^{3+}$ binding constant (log K) of 10 or more. In other implementations, the iron chelator may have a $Fe^{3+}$ binding constant (log K) of 11 or more, 12 or more, 13 or more, 14 or more, 15 or more 16 or more, 17 or more, and/or 1.8 or more. When more than one metal chelator is used, at least one metal chelator may have a high $Fe^{3+}$ binding constant. For example, a $Fe^{3+}$ binding constant (log K) of 10 or more, 11 or more, or 12 or more.

The oral care composition may be substantially liquid in character, such as a mouthwash or rinse, and may include additional ingredients common to liquid oral care compositions, such as carriers, humectants, surfactants, polymers, thickeners, antioxidants, preservatives, flavoring agents, sweeteners, colorants, pH modifiers, anti-calculus agents, and fluoride sources.

All ingredients used in the oral care compositions described herein may be orally acceptable. "Orally acceptable" means an ingredient which is present in the composition as described in an amount and form which does not render the composition unsafe, unpalatable, or otherwise unsuitable for use in the oral cavity. In addition, the additional ingredients should not substantially inhibit the efficacy of the antibacterial agent (chlorhexidine) or metal chelators described herein.

In various implementations of the present disclosure, the oral care composition includes an orally acceptable carrier. As used herein, an "orally acceptable carrier" refers to a material or combination of materials that are safe for use in the oral care compositions of the present disclosure while retaining significant efficacy for the antibacterial agent(s). In certain implementations, the carrier is specifically selected to ensure that there is no substantially reduction in efficacy for the antibacterial agent(s).

The oral care composition may be aqueous or non-aqueous, or may include a mixture of liquids as the carrier. For example, the carrier may be water, and the water may be deionized and free of organic impurities. Water may make up the balance of the oral care composition and may include from about 10 weight % to about 90 weight %, e.g., from about 40 weight % to about 70 weight % water, based on the total weight of the oral care composition. This amount of water may include free water which is added plus that amount which is introduced with other materials, such as with sorbitol or any other components of the oral care composition.

In other implementations, the carrier may be a water-alcohol mixture. The ratio of water to alcohol may be in the range of from about 1:1 to about 20:1, preferably from 3:1 to 20:1, and most preferably about 17:3, by weight. The total amount of water alcohol mixture may be from about 70 weight % to about 99.9 weight %, based on the total weight of the oral care composition. The pH of the oral care composition may be from about 4.5 to about 9, and typically, from about 5.5 to 8. The of the oral care composition is preferably in the range of from about 6 to about 8.0.

In certain implementations, the oral care composition may include one or more humectants.

Humectants may reduce evaporation and lower water activity. Certain humectants may impart desirable sweetness or flavor to the compositions. The humectant may be a mixture of humectants, such as glycerin and sorbitol, and a polyhydric alcohol, such as propylene glycol, butylene glycol, hexylene glycol, polyethylene glycol. The oral care composition may include from 15 weight % to 70 weight % or from 30 weight % to 65 weight % humectant, based on a total weight of the oral care composition.

The oral care composition may include one or more surfactants. The surfactants may enhance a stability of the oral care composition, help clean the oral cavity surfaces through detergency, and provide foam upon agitation. In various implementations, suitable surfactants may function as a surface active agent, emulsifier, and/or foam modulator. Any orally acceptable surfactant, most of which are anionic, nonionic, cationic, or amphoteric, may be used. A combination of surfactants may also be used.

The surfactants may include anionic surfactants. For example, water-soluble salts of higher fatty acid monoglyceride monosulfates, such as the sodium salt of the monosulfated monoglyceride of hydrogenated coconut oil fatty acids, such as sodium N-methyl N-cocoyl taurate, sodium cocomo-glyceride sulfate; higher alkyl sulfates, such as sodium lauryl sulfate; higher alkyl-ether sulfates, such as sodium laureth-2 sulfate; higher alkyl aryl sulfonates, such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. The anionic surfactant may be selected from sodium lauryl sulfate and sodium ether lauryl sulfate. The anionic surfactant may be present in an amount which is effective, e.g., >0.001% by weight of the formulation, but not at a concentration which would be irritating to the oral tissue, e.g., 1%, and optimal concentrations depend on the particular formulation and the particular surfactant. For example, the anionic surfactant may be present at from about 0.03 weight % to about 0.5 weight % based on the total weight of the oral care composition.

The surfactants may include cationic surfactants, such as derivatives of aliphatic quaternary ammonium compounds having one long alkyl chain containing 8 to 18 carbon atoms, such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Certain cationic surfactants may also act as germicides.

The surfactants may include nonionic surfactants, such as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. For example, the oral care composition may include a nonionic surfactant selected from polaxamers (e.g., polaxamer 407), polysorbates (e.g., polysorbate 20), polyoxyl hydrogenated castor oils (e.g., polyoxyl 40 hydrogenated castor oil), and mixtures thereof.

The surfactants may include zwitterionic surfactants, such as derivatives of aliphatic quaternary ammonium, phosphonium, and sulfonium compounds, in which the aliphatic radicals can be straight chain or branched, and wherein one of the aliphatic substituents contains 8 to 18 carbon atoms and one contains an anionic water-solubilizing group, e.g., carboxy, sulfonate, sulfate, phosphate or phosphonate.

Illustrative examples of the surfactants suited for inclusion into the oral care composition include, but are not limited to, sodium alkyl sulfate, sodium lauroyl sarcosinate, cocoamidopropyl betaine and polysorbate 20, and combinations thereof.

In some implementations, the oral care composition includes from about 0.1% to about 5.0% surfactant based on a total weight of the oral care composition. For example, the oral care composition includes from about 0.3 weight % to about 3.0 weight % surfactant or from about 0.5 weight % to about 2.0 weight % surfactant.

The oral care compositions may include one or more polymers or polymeric agents, such as polyethylene glycols, polyvinylmethyl ether maleic acid copolymers, polysaccharides cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. For example, the oral care composition may include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of 30,000 to 3,000,000, most preferably 30,000 to 800,000, These copolymers are available for example as Gantrez. e.g., AN 139 (M.W. 500,000), AN 119 (M.W. 250,000) and S-97

Pharmaceutical Grade (M.W. 700,000) available from ISP Technologies, Inc., Bound Brook, N.J. 08805.

Other usable polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Generally suitable are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of usable polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of 1,000 to 2,000,000. Another useful class of polymeric agents includes polyamino acids, particularly those containing proportions of anionic surface-active amino acids such as aspartic acid, glutamic acid and phosphoserine.

In certain implementations, such as toothpastes, the oral care composition may include thickening agents or thickeners, Orally acceptable thickening agents may be used to provide a desirable consistency or to stabilize or enhance the performance of the oral care composition. The thickening agent may include carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums, such as karaya, gum arabic, and gum tragacanth can also be used. Colloidal magnesium aluminum silicate or finely divided silica can be used as component of the thickening composition to further improve the composition's texture. The oral care composition may include from about 0.5 weight % to about 5 weight based on the total weight of the oral care composition.

The oral care composition may include one or more additional antibacterial agents or preservatives. In some implementations, the preservatives improve an antimicrobial characteristic of the oral care composition to improve storage life or prevent decay. In other implementations, the one or more additional antibacterial agents or preservatives are non-metal.

In certain implementations, the one or more antibacterial agents or preservatives include at least one of sodium benzoate, methyl paraben, ethyl paraben, triclosan, stannum salts, and combinations thereof.

The oral care composition may include an effective amount of antibacterial agents or preservatives. For example, the oral care composition may include an amount of antibacterial agents or preservatives effective to reduce spoilage of the oral care composition during storage or use.

The oral care composition may include one or more flavoring agents. Useful flavoring agents include any material or mixture of materials operable to enhance the taste of the oral care composition. Any orally acceptable natural or synthetic flavoring agent may be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methyl salicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, x-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA) and mixtures thereof. In some implementations, the oral care composition includes from about 0.01% to about 1% flavoring agents based on a total weight of the oral care composition.

The oral care composition may also include one or more sweeteners. Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and mixtures thereof. Some implementations may include one or more sweeteners. In some implementations, the oral care composition includes from about 0.005% to about 1% sweeteners based on a total weight of the oral care composition.

The oral care composition may include colorants. Colorants, such as dyes or pigments, may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indane-dione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylatnino)-phenyl]-(4-hydroxy-2-sulfoniumphenyl)-methylene}-[1-(N-ethyl-N-p-sulfobenzyl)-DELTA-3,5-cycl-ohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants, if included, are present in very small quantities.

The oral care composition may also include one or more pH modifying agents. The pH modifying agents among those useful herein include acidifying agents to lower pH, basifying agents to raise pH and buffering agents to control pH within a desired range. Any orally acceptable pH modifying agent may be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range. In some implementations, the oral care composition includes from about 0.01% to about 10% pH modifier agents based on a total weight of the oral care composition.

The oral care composition may include one or more anti-calculus or calcium chelating agents able to complex calcium found in the cell walls of the bacteria. Binding of this calcium weakens the bacterial cell wall and augments bacterial lysis. Another group of agents suitable for use as calcium chelating or anti-calculus agents are soluble pyrophosphates salts. The pyrophosphate salts may be any of the alkali metal pyrophosphate salts, such as tetra alkali metal pyrophosphate, dialkali metal diacid pyrophosphate, trialkali metal monoacid pyrophosphate, and mixtures thereof, wherein the alkali metals are sodium or potassium. The pyrophosphate salts may be useful in both their hydrated and unhydrated forms. The oral care composition may include an effective amount of pyrophosphate salts.

The oral care composition may include one or more fluoride ion sources, e.g., soluble fluoride salts. A wide variety of fluoride ion-yielding materials may be employed as sources of soluble fluoride. Examples of suitable fluoride ion-yielding materials include, but are not limited sodium fluoride, potassium fluoride, sodium monofluorophosphate, sodium fluorosilicate, ammonium fluorosilicate, amine fluoride, ammonium fluoride, and combinations thereof. The fluoride ion source may include stannous fluoride, sodium fluoride, sodium monofluorophosphate as well as mixtures thereof. Where the oral care composition includes calcium salts, the fluoride salts are preferably salts wherein the fluoride is covalently bound to another atom, e.g., as in sodium monofluorophosphate, rather than merely ionically bound, e.g., as in sodium fluoride. The oral care composition may include an amount of fluoride ion sources sufficient to release up to about 0.13 weight %, preferably from about 0.0013 weight % to about 0.1 weight %, and most preferably about 0.0013 weight % to about 0.05 weight % fluoride ions, based on the total weight of the oral care composition.

Example 2

Table 3 illustrates a mouthwash according to some implementations of the present disclosure.

TABLE 3

| Ingredients | Wt. % |
| --- | --- |
| Chlorhexidine | 0.05-0.5% |
| Metal Chelator | 0.01-5% |
| Water | 40-99% |
| Additional Oral Care ingredients | 15% or less |

The exemplary composition described in Table 3 (above) may be prepared according to conventional methods known to those skilled in the art. In particular, the exemplary compositions are prepared to prevent CHX-caused staining when the oral care composition is applied to teeth, especially when applied to teeth surfaces at least daily, for a period of at least one of 1 day, 2 days, 1 week, 2 weeks, 3 weeks, 4 weeks, 1 month, and 2 months.

Example 3

Table 4 illustrates the effects of a metal chelator on CHX-caused staining when incorporating into an oral care composition including CHX according to implementations of the present disclosure. In particular, Table 4 illustrates the $\Delta W^*$ for 5 oral care compositions containing CHX and measured similarly as described above. The more positive the value of $\Delta W^*$, the darker the tooth color is.

Oral Care Composition #1 is a commercially available antimicrobial oral rinse with 0.12% chlorhexidine gluconate. Oral Care Compositions #2-#5 are the same as Oral Care Composition #1 except they include the specified amounts (by weight) of a metal chelator.

TABLE 4

| Treatment | Cycle 0 | Cycle 2 | Cycle 4 | Cycle 6 | Cycle 8 | Cycle 10 | Cycle 12 | Cycle 14 |
| --- | --- | --- | --- | --- | --- | --- | --- | --- |
| Oral Care Comp. #1 | 0 | 3.01 | 3.92 | 5.14 | 5.36 | 5.57 | 5.96 | 6.07 |
| Oral Care Comp. #2 + 0.2% Glutamic acid | 0 | 1.90 | 2.33 | 2.56 | 2.51 | 2.63 | 2.91 | 2.87 |
| Oral Care Comp. #3 + 1% Glutamic acid | 0 | 1.59 | 2.53 | 3.47 | 3.49 | 3.47 | 3.78 | 3.75 |
| Oral Care Comp. #4 + 0.2% Aspartic acid | 0 | 3.02 | 4.11 | 4.67 | 4.72 | 4.41 | 5.52 | 5.72 |
| Oral Care Comp. #5 + 1% Aspartic acid | 0 | 1.70 | 2.31 | 3.03 | 2.91 | 3.07 | 3.42 | 3.49 |

As illustrated in Table 4, the addition of a metal chelator reduces an amount of CHX-based staining. In particular, as illustrated in Table 4, the addition of glutamic acid and aspartic acid to an oral care composition containing CHX significantly reduced the amount of CHX-staining as evidenced by the reductions in the $\Delta W^*$ value. Addition of 0.2 weight % glutamic acid and 1 weight % aspartic acid were the best performers when combined with a CHX-containing commercially available oral care rinse (0.12% chlorhexidine gluconate).

The present disclosure has been described with reference to exemplary implementations. Although a few implementations have been shown and described, it will be appreciated by those skilled in the art that changes may be made in these implementations without departing from the principles and spirit of preceding detailed description. It is intended that the present disclosure be construed as including all such modifications and alterations insofar as they come within the scope of the appended claims or the equivalents thereof.

What is claimed is:

1. An oral care composition, comprising:
    0.12% chlorhexidine, based on a total weight of the oral care composition; and
    an effective amount of metal chelator, and the metal chelator is selected from glutamic acid in an amount of 0.2% and aspartic acid in an amount of 1%, wherein the amounts are based on a total weight of the oral care composition.

2. The oral care composition of claim 1, further comprising one or more additional oral care ingredients selected from: a carrier, a humectant, surfactants, polymers, thickeners, antioxidants, preservatives, flavoring agents, sweeteners, colorants, pH modifiers, anti-calculus agents, fluoride sources, and wherein all the ingredients of the oral care composition are orally acceptable.

3. A method of reducing staining by an oral care composition, comprising:
    providing to a tooth surface an effective amount of a composition of claim 1.

4. The method of claim 3, wherein the oral care composition is applied at least daily.

* * * * *